US005895819A

United States Patent [19]
Hagi

[11] Patent Number: 5,895,819
[45] Date of Patent: Apr. 20, 1999

[54] ENZYME SUBSTRATE

[75] Inventor: Norio Hagi, Kanagawa, Japan

[73] Assignee: Tosoh Corporation, Yamaguchi, Japan

[21] Appl. No.: 08/881,360

[22] Filed: Jun. 24, 1997

[30]  Foreign Application Priority Data

Jun. 24, 1996  [JP]  Japan ................................ 8-162852

[51] Int. Cl.$^6$ .............................. C07F 9/06; C07F 9/22
[52] U.S. Cl. ..................... 549/218; 562/11; 435/7.9; 435/7.21
[58] Field of Search ........................... 435/7.9, 7.21, 435/967, 968; 549/218; 562/11

[56] References Cited

U.S. PATENT DOCUMENTS 5,143,825  9/1992  Chacko et al. ....................... 435/7.9

Primary Examiner—Alan L. Rotman
Assistant Examiner—Charanjit S. Aulakh
Attorney, Agent, or Firm—Sughrue, Mion, Zinn, Macpeak & Seas, PLLC

[57] ABSTRACT

An enzyme substrate is disclosed which comprises a phosphoric ester and an organic acid or a salt thereof having a zinc chelating stability factor constant (log K) of from 8 to 14 in an aqueous solution having an ionic strength of 0.1 at 20 to 25° C. A reagent kit for an enzyme activity assay, a reagent kit for an immunoassay, a method for stabilizing a phosphoric ester, a method for producing a stabilized phosphoric ester.

11 Claims, 6 Drawing Sheets

ENZYME SUBSTRATE

FIELD OF THE INVENTION

The present invention relates to an improved enzyme substrate, a method for producing the improved enzyme substrate, a reagent kit for an enzyme activity assay containing the improved enzyme substrate, and the like. Also, the present invention provides excellent enzyme substrates and the like which have improved stability and can be used, for example, in enzyme immunoassay.

BACKGROUND OF THE INVENTION

In recent years, amounts of trace protein and the like contained in biological samples, such as sera, urine and the like, can be measured by an enzyme immunoassay, such as so-called sandwich immunoassay, competitive immunoassay and the like, using antibodies and antigens. For example, in the sandwich immunoassay, a sandwich complex (immobilized antibody—antigen—labeled antibody) in correlation with the amount of an antigen to be measured (referred to as an "analyte") is formed from an immobilized monoclonal antibody (immobilized antibody) specific for the analyte and an enzyme-linked monoclonal antibody which is different from the above monoclonal antibody but specific for the analyte (labeled antibody), a labeled antibody remained after the sandwich complex formation is separated, and then the amount of the enzyme in the sandwich complex is measured based on its activity to finally estimate the amount of the analyte.

Enzyme substrates for use in respective enzyme reactions are provided generally in the form of solution or freeze-dried powder. When an enzyme reaction is carried out, the substrate solution is used directly or after dilution or the freeze-dried powder is used after making it into a solution by adding water or the like. However, when the enzyme substrate is deteriorated, it causes bad influences upon the results of enzyme activity measurement, such as poor reproducibility and the like. In consequence, for manufacturers who produce and provide enzyme substrates, it is necessary to provide enzyme substrates which are stable for a prolonged period of time so that their reactivity with enzymes does not change.

In the enzyme immunoassay described above, enzymes are used as labels for measuring analytes. In addition, other techniques are frequently used such as a method in which an enzyme amount in a body fluid is determined by measuring its enzyme activity.

For example, JP-A-2-188578 (the term "JP-A" as used herein means an "unexamined published Japanese patent application") discloses that enzyme substrates are stabilized under alkaline conditions. However, since each enzyme has its own optimum pH range for generating its activity, the use of an enzyme substrate stabilized under alkaline conditions in this manner directly in the measurement of enzyme activity will reduce the enzyme activity itself when the alkaline pH does not coincide with the optimum pH of the enzyme to be measured, thereby causing a problem of decreased measuring accuracy. It is possible as a matter of course to adjust the pH value of a substrate solution stabilized under alkaline conditions to the optimum pH of the target enzyme, but it requires an additional step for adjusting a pH value prior to the measurement of enzyme activity.

In addition, U.S. Pat. No. 5,143,825 discloses a method for stabilizing an enzyme solution, which comprises adding a metal chelating agent, such as EDTA, EGTA or the like, to an enzyme substrate solution. In this method, 4-methylumbelliferone phosphoric acid or a salt thereof is stabilized by capturing metal ions which non-enzymatically hydrolyze the substrate. However, when 4-methylumbelliferone phosphoric acid or a salt thereof is used in this method as the substrate of alkaline phosphatase or the like which is frequently used in immunoassays but requires magnesium and zinc ions for generating its activity, these ions are also captured by the chelating agent to inhibit the enzyme activity, so that it is necessary to carry out an additional step such as removal of the chelating agent prior to use of the substrate solution.

In this connection, it is possible to improve stability of an enzyme substrate by freeze-drying or the like as compared with storage as a solution. However, even in the freeze-drying treatment, it would be convenient for users if an enzyme substrate capable of maintaining its quality more stably for more prolonged period of time could be provided. That is, this is because, since the freeze-dried enzyme substrate is dissolved in an appropriate solution prior to use, a large amount of stock solution can be prepared and stored by improving the storage stability of the substrate after dissolving even if the substrate is freeze-dried.

SUMMARY OF THE INVENTION

For providing a more stable enzyme substrate, the inventor of the present invention has conducted intensive studies and found as the result that phosphoric esters which are used as the substrates of hydrolases such as alkaline phosphatase and the like frequently used as labels in the field of immunoassay and the like can be stabilized by allowing citric acid and/or succinic acid to coexist in the enzyme substrate system. The present invention has been accomplished on this finding.

Accordingly, the present invention provides an enzyme substrate which comprises a phosphoric ester and an organic acid or a salt thereof having a zinc chelating stability factor constant (log K) of from 8 to 14 in an aqueous solution having an ionic strength of 0.1 at 20 to 25° C.

Furthermore, the present invention provides a reagent kit for an enzyme activity assay which comprises the above enzyme substrate.

Moreover, the present invention provides a reagent kit for an immunoassay using an enzyme as a label which comprises the enzyme substrate.

Still furthermore, the present invention provides a method for stabilizing a phosphoric ester which comprises allowing to coexist an organic acid or a salt thereof having a zinc chelating stability factor constant (log K) of from 8 to 14 in an aqueous solution having an ionic strength of 0.1 at 20 to 25° C.

Still moreover, the present invention provides a method for producing a stabilized phosphoric ester which comprises adding an organic acid or a salt thereof having a zinc chelating stability factor constant (log K) of from 8 to 14 in an aqueous solution having an ionic strength of 0.1 at 20 to 25° C.

DETAILED DESCRIPTION OF THE INVENTION

The organic acid or the salt thereof (hereinafter often simply referred to as "the organic acid") having a zinc chelating stability factor constant (log K) of from 8 to 14 in an aqueous solution having an ionic strength of 0.1 at 20 to 25° C. captures metal ions which non-enzymatically decompose phosphoric esters or salts thereof such as 4-methylumbelliferone phosphoric acid or a salt thereof (hereinafter simply referred to as "4MUP"), p-nitrophenylphosphoric acid or a salt thereof (hereinafter simply referred to as "PNPP") and the like, thereby preventing deterioration of their qualities and the like during storage. Since the stability factor constant (log K) of EDTA under such conditions is about 16.5, the use of an organic acid having smaller metal ion capturing ability than that of EDTA renders possible the use of the phosphoric ester, such as 4MUP or the like, as the substrate of an enzyme without causing capture of metal ions which are necessary for generating enzyme activity.

Examples of the organic acid for use in the present invention include citric acid and oxalic acid having a stability factor constant of about 11 and succinic acid having a stability factor constant of about 13. The organic acids, such as citric acid, oxalic acid, succinic acid and the like, may be used alone or as a mixture of two or more. The organic acid is preferably at least one of citric acid and succinic acid or a salt thereof.

Examples of the salt of the organic acid include a sodium salt and a potassium salt. Also, the salts of the organic acid of the present invention include hydrates thereof.

Preferably, the organic acid may be added prior to long-term preservation of 4MUP and the like, but it can also be added at various stages. For example, it may be added most preferably just after the preparation of a 4MUP stock solution or, when the solution is freeze-dried, just before its freeze-drying treatment, although the effect of the present invention can be expected when the organic acid is added at least prior to enzyme activity measurement.

The amount of the organic acid(s) to be added to and to be coexisted with phosphoric esters, such as 4MUP, PNPP and the like, is not particularly limited, but it may be preferably from 0.1 to 1,000 mM in total, more preferably from 1 to 100 mM in total.

The enzyme substrate of the present invention may be an aqueous solution or a dry material.

As shown in the following Examples, the coexistence of citric acid and succinic acid does not exert influences upon the measurement of enzyme activities so that the reactivity of an enzyme with 4MUP, PNPP or the like does not change. In consequence, it is possible to provide a stabilized high quality reagent kit from which improved reproducibility can be expected, when the phosphoric ester, such as 4MUP, PNPP or the like, produced by adding the organic acid is used as a composing reagent of a kit for use in the measurement of enzyme activity effected, for example, by an enzyme immunoassay or the like.

Thus, according to the present invention, it is possible to stabilize enzyme substrates for a prolonged period of time in comparison with the prior art means. As a result, it is possible to provide a phosphoric ester, such as 4MUP, PNPP or the like, in the form of a solution having the same stability of its freeze-dried form which is provided in the prior art in order to improve its stability. In consequence, according to the present invention, an operation, such as freeze-drying or the like, which is complex and difficult to control in each step can be omitted, and 4MUP or PNPP can be stored stably for a prolonged period of time even in the form of solution. Because of this, it is not necessary to use an enzyme substrate solution by preparing its required amount at the time of its use in order to avoid decrease in the reproducibility, so that the inconvenience of preparing the substrate every time of its use can be resolved. As a matter of course, the solution of phosphoric acid, such as 4MUP, PNPP or the like, produced by the present invention can be freeze-dried with no objection, and, when the enzyme substrate provided by the present invention is freeze-dried, its stability can be improved particularly after dissolution of the dry product.

The present invention can markedly improve the stability of the phosphoric esters, such as 4MUP, PNPP and the like, commonly used in the enzyme activity measurement of alkaline phosphatase which is frequently used in enzyme immunoassay, so that the invention is useful for improving the long-term stability of enzyme substrates in the field of enzyme immunoassay.

The present invention will now be illustrated in greater detail with reference to Examples, but it should be understood that the invention is not construed as being limited thereto. Unless otherwise indicated, all the percents and ratios are by weight.

EXAMPLE 1

Effect of Citric Acid and/or Succinic Acid (Citric Acid and/or Succinic Acid Ion) on Hydrolysis Rate of 4MUP Production of Enzyme Substrate:

A 44.46 g portion of 2-amino-2-methyl-1-propanol (produced by Nakalai Kagaku) and 1 g of sodium azide (produced by Nakalai Kagaku) were put into a container and made up to about 900 ml by adding distilled water. The resulting solution was adjusted to pH 10 with concentrated hydrochloric acid while monitoring with a pH meter and then the total volume was adjusted to 1 liter by adding purified water.

The thus prepared solution was mixed with 256.2 mg of 4-methylumbelliferone phosphoric acid (produced by JBL, U.S.A.) to obtain a 1 mM 4MUP solution (hereinafter referred to as "base substrate").

To the base substrate was added a manganese solution (produced by Nakalai Kagaku), a zinc solution (produced by Nakalai Kagaku), a cadmium solution (produced by Nakalai Kagaku), an aluminum solution (produced by Nakalai Kagaku), an iron solution (produced by Nakalai Kagaku), a cobalt solution (produced by Nakalai Kagaku), a nickel solution (produced by Nakalai Kagaku), a magnesium solution (produced by Nakalai Kagaku) or a lead solution (produced by Nakalai Kagaku) to a final concentration of 100 ppm, thereby obtaining a control solution.

Measurement of Substrate Stability:

Each of the solutions prepared above was put into an incubator of 4° C., 25° C., 35° C. or 45° C., and a portion of the solution was sampled at predetermined intervals, diluted 10 times with a dilution solution (0.14 M phosphate buffer, 0.1 M EDTA (produced by Nakalai Kagaku), 0.1% sodium azide, pH 9.1) and then measured by a fluorescence spectrophotometer (Hitachi F2000, a 1 cm glass square cell was used). The measurement by the fluorescence spectrophotometer was carried out at room temperature at an excitation wavelength of 363 nm (band pass 5 nm) and a fluorescence wavelength of 447 nm (band pass 5 nm), and the results were calculated as a relative fluorescence strength by comparing them with the results of the measurement of known concentrations of 4MU (serial dilutions prepared using a dilution solution (0.14 M phosphate buffer, 0.1 M EDTA (disodium dihydrate, produced by Nakalai Kagaku), 0.1% sodium azide, pH 9.1) used for measuring concentration of 4MU formed by hydrolysis of 4MUP.

Figure 1:
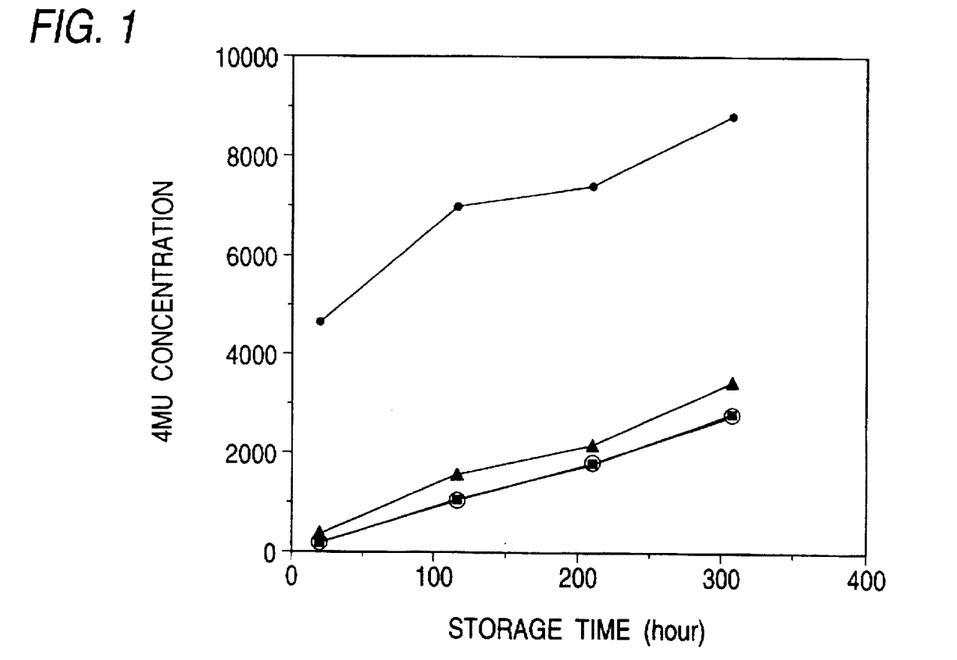
FIG. 1 is a graph showing one of the results of Example 1, in which a base substrate and control solutions including a manganese, zinc or cadmium solution were used. In the drawing, the 4MU concentration is plotted as ordinate and the preservation time (hour) as abscissa, and the results are indicated by "o" on the base substrate, by "." on the control solution containing manganese, by "▲" on the control solution containing zinc and by "■" on the control solutions containing cadmium.
Figure 2:
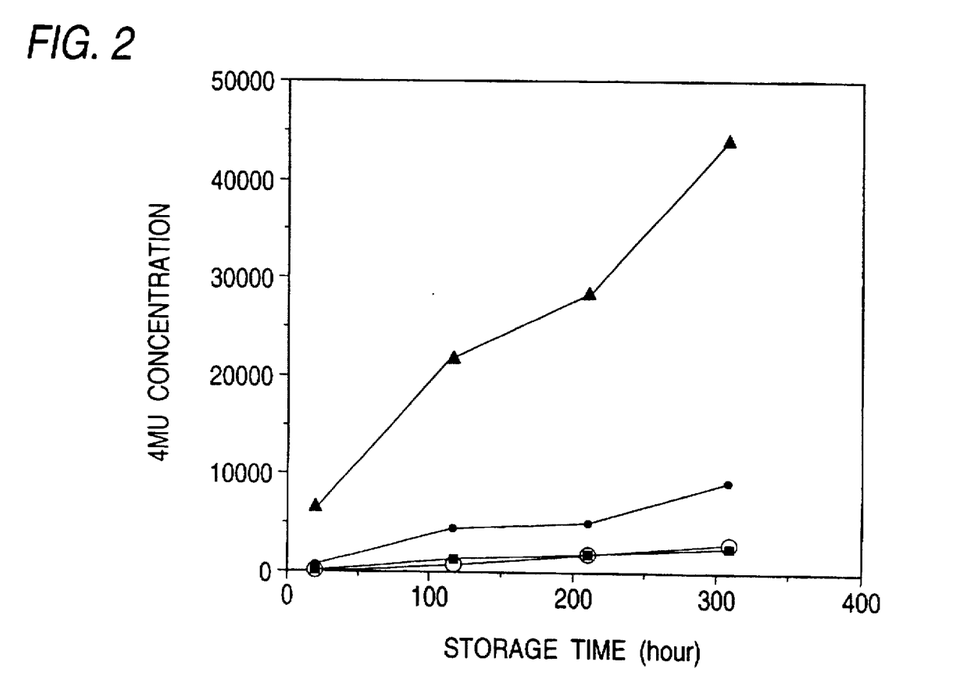
FIG. 2 is a graph showing one of the results of Example 1, in which the base substrate and control solutions including an aluminum, iron or cobalt solution were used. In the drawing, the 4MU concentration is plotted as ordinate and the preservation time (hour) as abscissa, and the results are indicated by "o" on the base substrate, by "." on the control solution containing aluminum, by "▲" on the control solution containing iron and by "■" on the control solutions containing cobalt.
Figure 3:
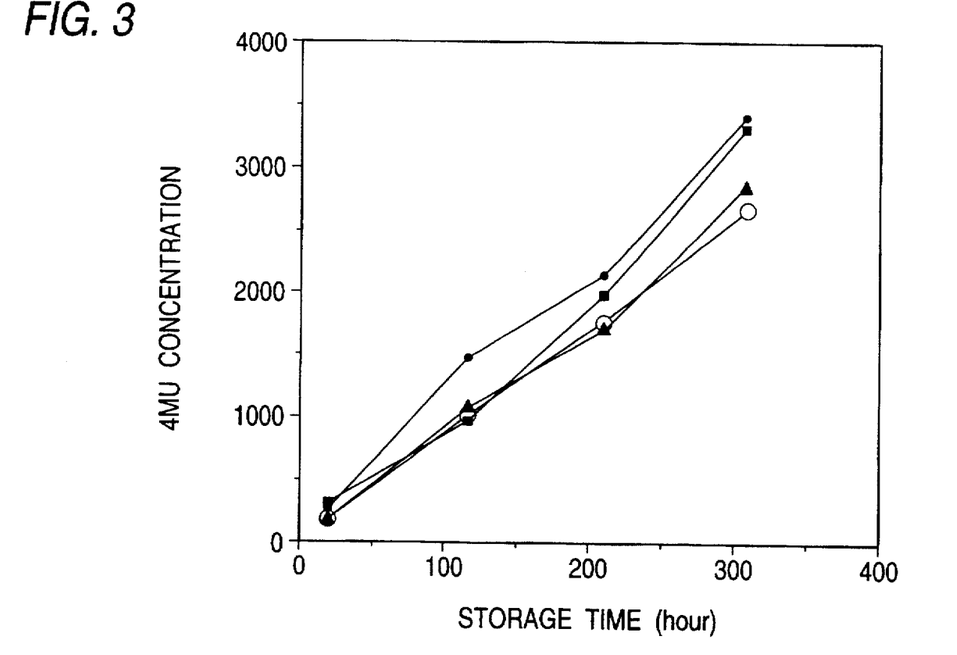
FIG. 3 is a graph showing one of the results of Example 1, in which the base substrate and control solutions including a nickel, magnesium or lead solution were used. In the drawing, the 4MU concentration is plotted as ordinate and the preservation time (hour) as abscissa, and the results are indicated by "o" on the base substrate, by "." on the control solution containing nickel, by "▲" on the control solution containing magnesium and by "■" on the control solutions containing lead.
Figure 4:
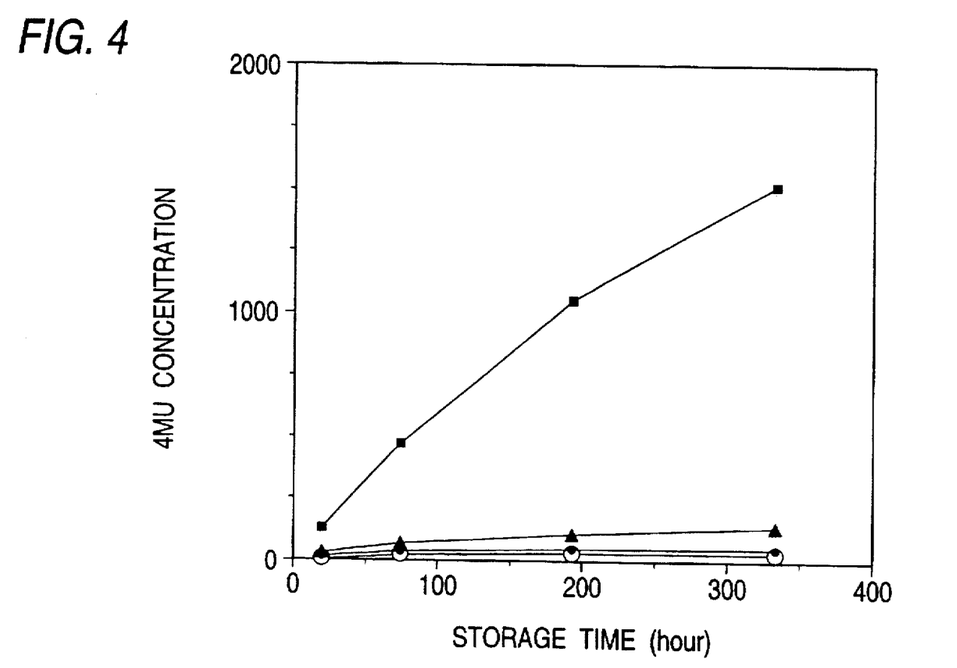
FIG. 4 is a graph showing one of the results of Example 2, in which the base substrate and a control solution containing iron were stored at 4° C. In the drawing, the 4MU concentration is plotted as ordinate and the preservation time (hour) as abscissa, and the results are indicated by "o" on the base substrate, by "." on the control solution containing 1 ppm of iron, by "▲" on the control solution containing 10 ppm of iron and by "■" on the control solutions containing 100 ppm of iron.
Figure 5:
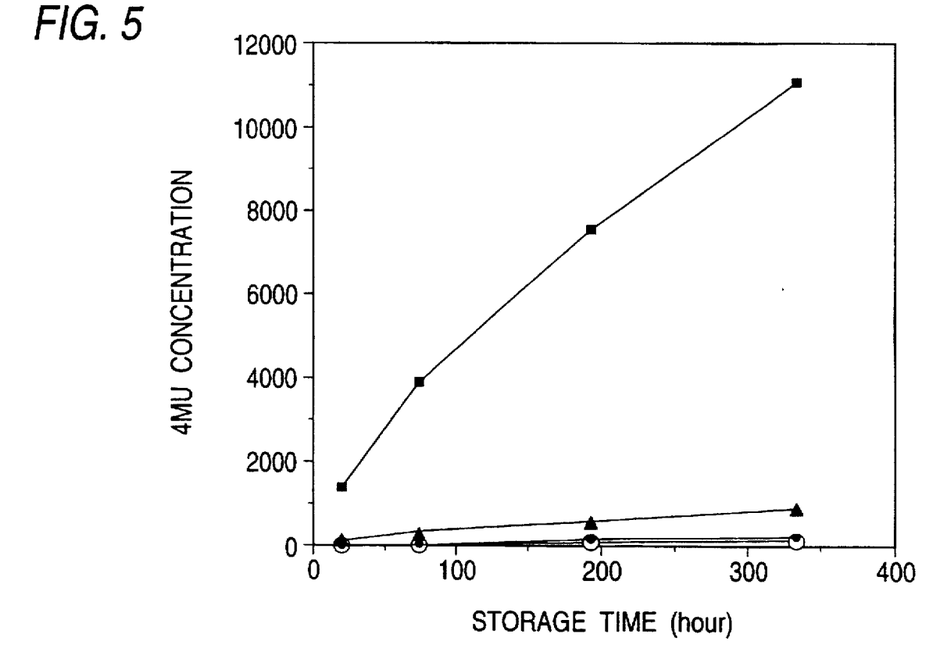
FIG. 5 is a graph showing one of the results of Example 2, in which the base substrate and a control solution containing iron were stored at 25° C. In the drawing, the 4MU concentration is plotted as ordinate and the preservation time (hour) as abscissa, and the results are indicated by "o" on the base substrate, by "." on the control solution containing 1 ppm of iron, by "▲" on the control solution containing 10 ppm of iron and by "■" on the control solutions containing 100 ppm of iron.
Figure 6:
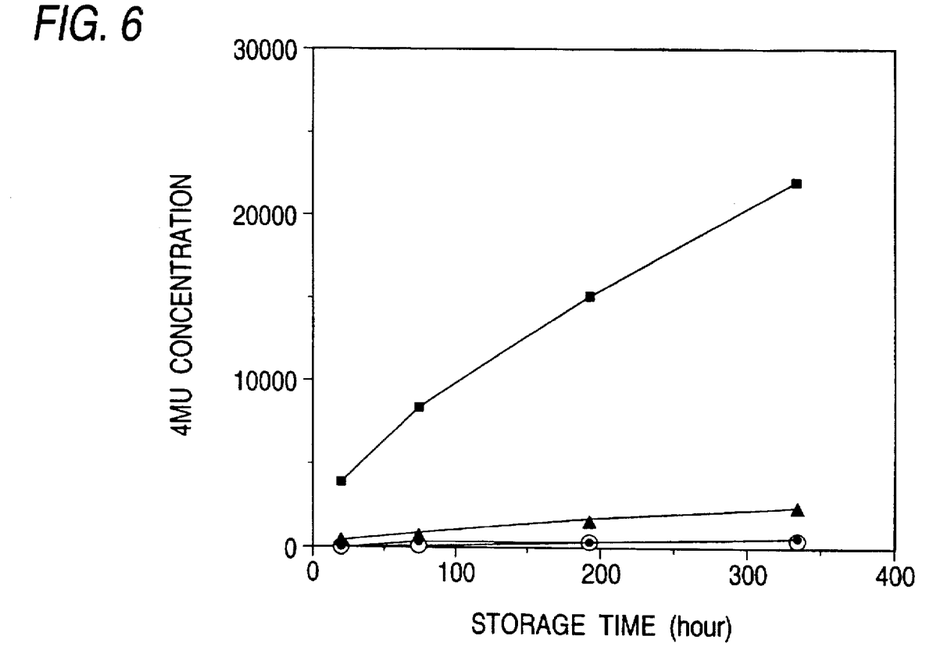
FIG. 6 is a graph showing one of the results of Example 2, in which the base substrate and a control solution containing iron were stored at 35° C. In the drawing, the 4MU concentration is plotted as ordinate and the preservation time (hour) as abscissa, and the results are indicated by "o" on the base substrate, by "." on the control solution containing 1 ppm of iron, by "▲" on the control solution containing 10 ppm of iron and by "■" on the control solutions containing 100 ppm of iron.
Figure 7:
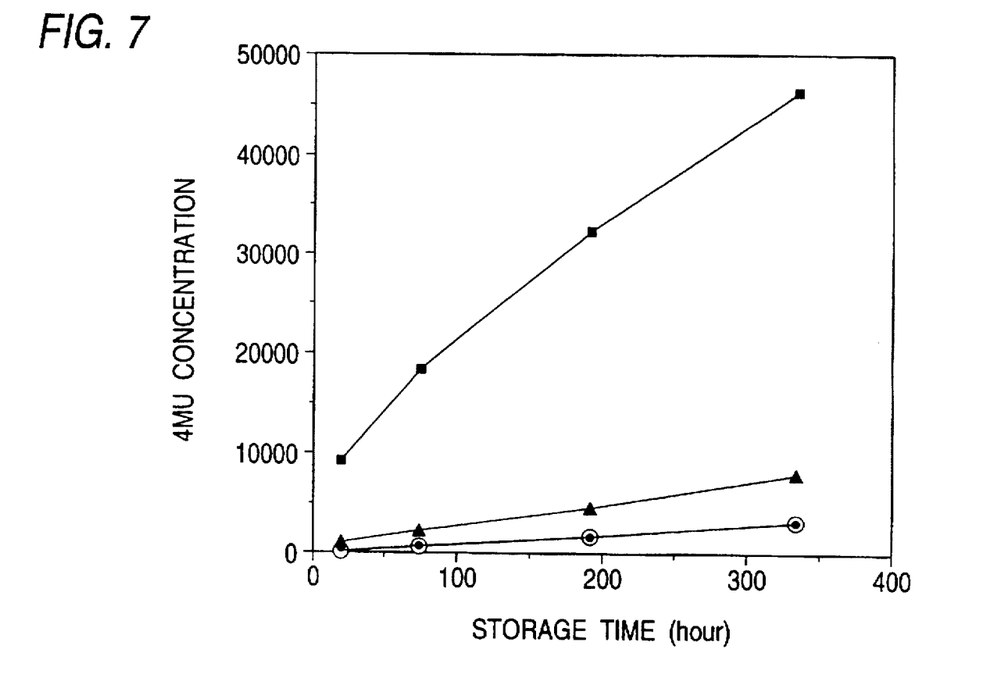
FIG. 7 is a graph showing one of the results of Example 2, in which the base substrate and a control solution containing iron were stored at 45° C. In the drawing, the 4MU concentration is plotted as ordinate and the preservation time (hour) as abscissa, and the results are indicated by "o" on the base substrate, by "." on the control solution containing 1 ppm of iron, by "▲" on the control solution containing 10 ppm of iron and by "■" on the control solutions containing 100 ppm of iron.

Examples of the results when incubated at 45° C. are shown in FIGS. 1 to 3. It can be seen from these results that the formation of 4MU is quick in the control solutions, particularly in the control solution to which the iron solution was added, in comparison with the base substrate, namely that the stability of 4MUP disappears (be hydrolyzed) in the coexistence of these metal ions. Also, when these solutions were incubated at 4° C., 25° C. and 35° C. (data not shown in drawings), the amount of formed 4MU decreased as the incubation temperature decreased, thus showing that the non-enzymatic formation of 4MU by hydrolysis of 4MUP in the coexistence of the metal ions is temperature-dependent.

EXAMPLE 2

Effect of Iron Ion Concentration on Hydrolysis of 4MUP

The base solution prepared in the same manner as in Example 1 and a control solution prepared by adding to the base solution an iron solution (produced by Nakalai Kagaku) to a final concentration of 1 ppm, 10 ppm or 100 ppm were incubated at certain temperatures for predetermined periods, and then the 4MU concentrations were measured using a fluorescence spectrophotometer in the same manner as described in Example 1. The results are shown in FIGS. 4 to 7. As is apparent from these drawings, degree of the formation of 4MU, namely non-enzymatic formation of 4MU by hydrolysis of 4MUP, increases depending on the concentration of iron ion.

EXAMPLE 3

Effect of Succinic Acid or Citric Acid on Hydrolysis of 4MUP

The base solution prepared in the same manner as in Example 1, a control solution prepared by adding to the base solution an iron solution (produced by Nakalai Kagaku) to a final concentration of 1 or 10 ppm and a substrate solution prepared by adding to the control solution succinic acid or citric acid to a final concentration of 10 mM (hereinafter referred to as "succinic acid-added substrate" or "citric acid-added substrate", respectively) were incubated at certain temperatures for predetermined periods, and then the 4MU concentrations were measured using a fluorescence spectrophotometer in the same manner as in Example 1.

Figure 8:
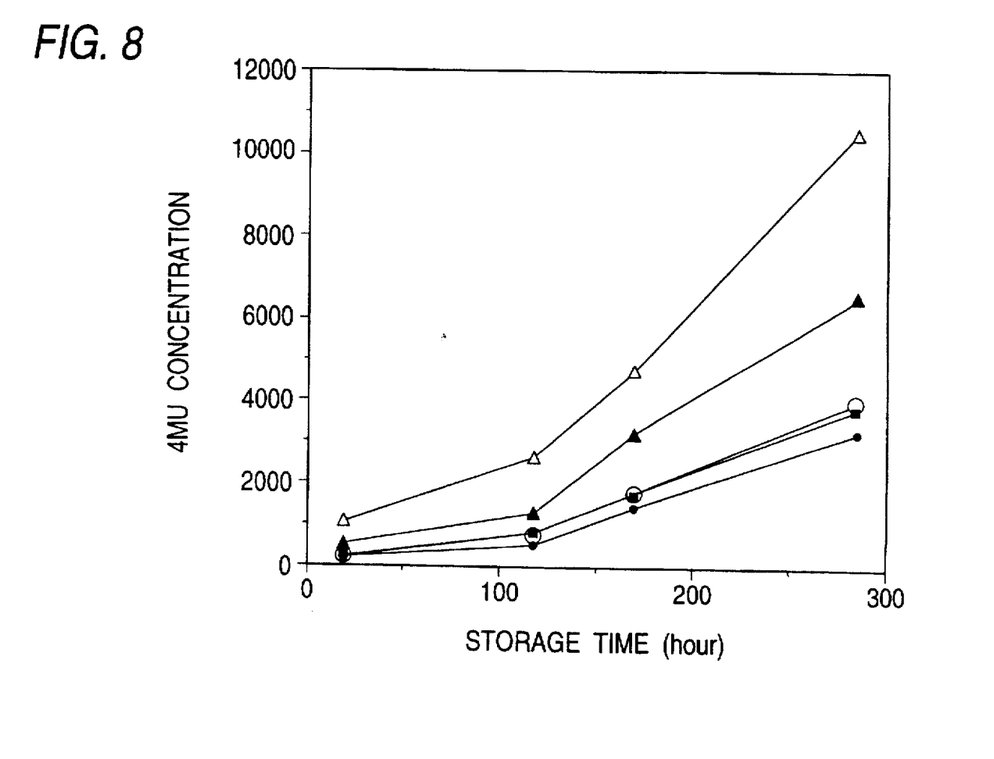
FIG. 8 is a graph showing one of the results of Example 3, in which respective samples were stored at 45° C. In the drawing, the 4MU concentration is plotted as ordinate and the preservation time (hour) as abscissa, and the results are indicated by "o" on the base substrate, by "Δ" on the control solution containing iron, by "." on the substrate to which succinic acid was added, by "▲" the substrate to which citric acid was added and by "■" on the substrate to which EDTA was added.

An example of the results when incubated at 45° C. is shown in FIG. 8. As is apparent from these results, formation of 4MU increases in the control solution in comparison with the base substrate, but the increment is inhibited in the citric acid-added substrate or succinic acid-added substrate.

EXAMPLE 4

Measurement of Enzyme Activity of Alkaline Phosphatase

Using the base solution prepared in the same manner as in Example 1, a control solution prepared by adding to the base solution an iron solution (produced by Nakalai Kagaku) to a final concentration of 1 ppm and a substrate solution prepared by adding to the control solution succinic acid, citric acid or EDTA to a final concentration of 10 mM (hereinafter referred to as "succinic acid-added substrate", "citric acid-added substrate" or "EDTA-added substrate", respectively) were prepared.

Figure 9:
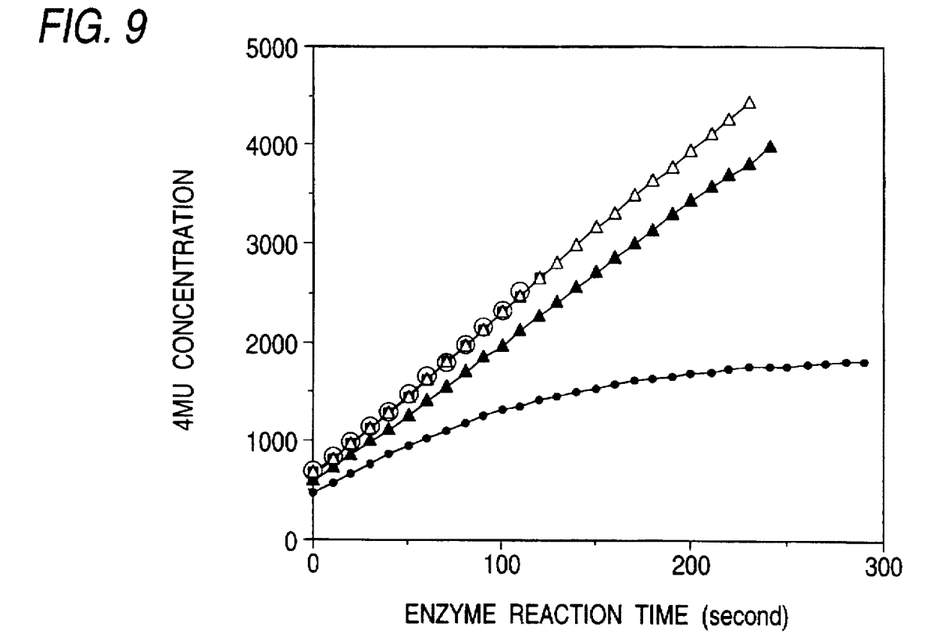
FIG. 9 is a graph showing the results of Example 4. In the drawing, the 4MU concentration is plotted as ordinate and the enzyme reaction time (second) as abscissa, and the results are indicated by "o" on the base substrate, by "■" on the control solution containing iron, by "▲" on the substrate to which succinic acid was added, by "Δ" on the substrate to which citric acid was added and by "." on the substrate to which EDTA was added.

A 20 µl portion of 50 mM Tris-HCl buffer (pH 7.5) containing 0.1% bovine serum albumin (produced by Sigma), in which commercially available alkaline phosphatase (produced by Sigma) had been dissolved to a final concentration of 14 g/ml, was added to 1.5 ml of each of the substrate solutions, and then the 4MU concentration was measured in the same manner as in Example 1. In this case, the measurement was carried out under a temperature condition of 37° C. The results are shown in FIG. 9. As is apparent from FIG. 9, the 4MU concentration was increased, namely the enzyme activity to produce 4MU was not inhibited, in all cases of the base substrate, control solution, succinic acid-added substrate and citric acid-added substrate. In the case of the EDTA-added substrate, on the other hand, increment of the 4MU was inhibited due to inhibition of the enzyme activity.

Based on the results of this example and the results of Examples 1 to 3, it can be understood that the addition of the organic acids, such as succinic acid and the like, renders possible stable preservation of substrates, such as 4MUP and the like, without inhibiting the enzyme activity.

EXAMPLE 5

Enzyme Immunoassay of TSH (Preparation of Antibody-immobilized Solid Phase Beads)

Pellets of an ethylene-vinyl acetate copolymer (EVA) having an average diameter of 1.4 mm and an average length of 1.5 mm (produced by Tosoh Corp.) obtained by a water strand method were made into spherical beads in accordance with the method disclosed in U.S. Pat. No. 5,200,270, thermally fused with ferrite (produced by Tosoh Corp.) and then coated with glycidyl methacrylate (GMA). The thus obtained polymer-coated beads were treated with a sodium hydroxide/methanol solution for converting the epoxy group in the surface layer into diol by its ring opening.

Mouse anti-human TSH (thyroid-stimulating hormone) monoclonal antibody (first antibody) was immobilized on the thus obtained beads in the following manner. At first, 100,000 beads were subjected to an activation treatment in accordance with the method disclosed in U.S. Pat. No. 5,200,270, by vigorously stirring them in 25 ml of dry acetone containing 500 mg of N,N'-carbonyldiimidazole (CDI, produced by Tokyo Kasei Kogyo) for 30 minutes at room temperature in an atmosphere of nitrogen. The thus activated beads were washed, mixed with 2.5 mg/20 ml of mouse anti-human TSH monoclonal antibody and then shaken for 4 hours at room temperature for binding the antibody to the beads.

After washing, the beads were mixed with phosphate buffer (pH 7.0) containing 1.0% bovine serum albumin (BSA) to carry out a blocking treatment.

Bovine small intestine alkaline phosphatase was used as a labeled enzyme and conjugated with anti-human TSH monoclonal antibody (second antibody) in the usual way.

Using the thus prepared antibody-immobilized beads, an enzyme immunoassay of human TSH was carried out. At first, 12 of the antibody-immobilized beads were put into a plastic cup and mixed with 50 µl of the labeled antibody (second antibody). This was set on a measuring apparatus (AIA-1200, produced by Tosoh Corp.) equipped with a magnet in its lower part, and the enzyme immunoassay was started by adding 100 µl of a TSH solution having a concentration of 0 or 48 µIU/ml as the antigen solution. In order to progress the antigen-antibody reaction of TSH, incubation was carried out at 37° C. for 40 minutes while shaking the lower part magnet at about 83 strokes/min, and then the reaction container was washed with a washing solution (B/F separation).

After completion of the washing, a 100 µl portion of each of the substrate solutions prepared in Example 4 was distributed to carry out the enzyme reaction. The reaction was carried out at 37° C. for 3, 6 and 10 minutes while shaking the lower part magnet at about 83 strokes/min. After termination of the enzyme reaction by adding 500 µl of an enzyme reaction terminating dilution solution (0.14 M phosphate buffer, 0.1 M EDTA, 0.1% sodium azide, pH 9.1), the resulting reaction solution was diluted with the dilution solution in Example 1 and its fluorescence quantity was measured in the same manner as in Example 1.

Figure 10:
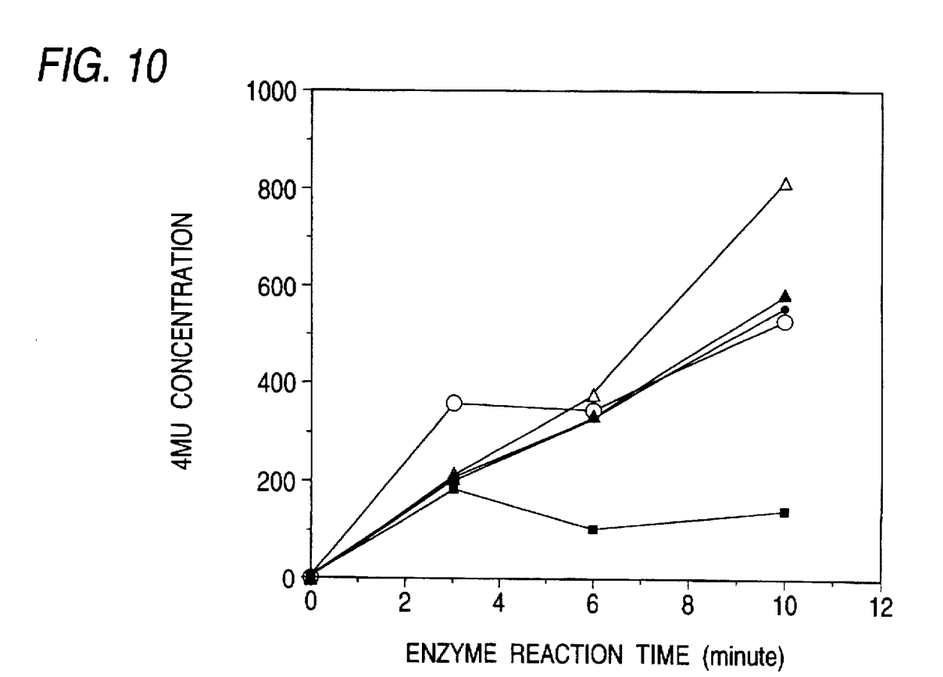
FIG. 10 is a graph showing one of the results of Example 5, in which TSH having a concentration of 0 μIU/ml was measured. In the drawing, the 4MU concentration is plotted as ordinate and the enzyme reaction time (minute) as abscissa, and the results are indicated by "o" on the base substrate, by "Δ" on the control solution containing iron, by "." on the substrate to which succinic acid was added, by "▲" on the substrate to which citric acid was added and by "■" on the substrate to which EDTA was added.
Figure 11:
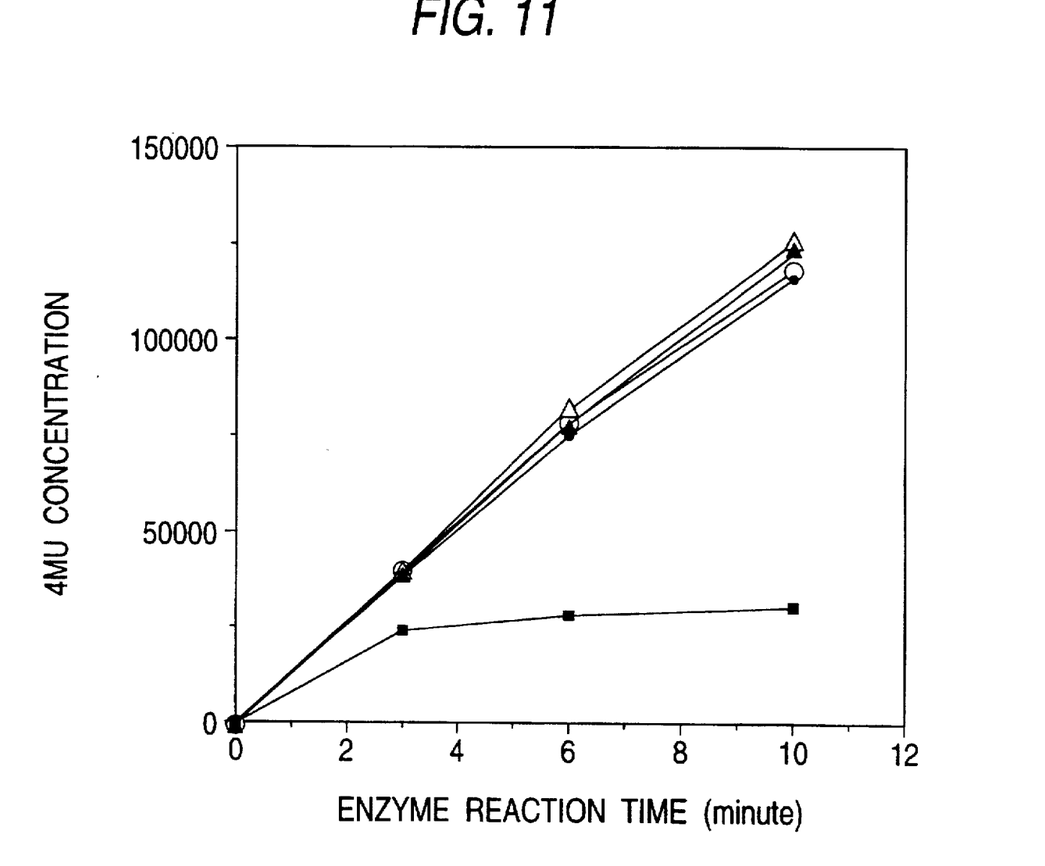
FIG. 11 is a graph showing one of the results of Example 5, in which TSH having a concentration of 50 μIU/ml was measured. In the drawing, the 4MU concentration is plotted as ordinate and the enzyme reaction time (minute) as abscissa, and the results are indicated by "o" on the base substrate, by "Δ" on the control solution containing iron, by "." on the substrate to which succinic acid was added, by "▲" on the substrate to which citric acid was added and by "■" on the substrate to which EDTA was added.

The results are shown in FIGS. 10 and 11. It can be found from these results that almost the same fluorescence quantity (amount of 4MU) can be obtained in the case of the base substrate, citric acid-added substrate and succinic acid-added substrate, namely that (1) the coexistence of citric acid and/or succinic acid does not inhibit the enzyme activity and (2) the coexistence of citric acid and/or succinic acid does not inhibit the immune reaction.

While the invention has been described in detail and with reference to specific examples thereof, it will be apparent to one skilled in the art that various changes and modifications can be made therein without departing from the spirit and scope thereof.

This application is based on application No. Hei 8-162852 filed in Japan, the entire content of which is incorporated hereinto by reference.

What is claimed is:

1. An enzyme substrate which comprises a phosphoric ester selected from 4-methylumbelliferone phosphoric acid or p-nitrophenylphosphoric acid or a salt thereof and at least one of citric acid and succinic acid or a salt thereof.

2. The enzyme substrate as claimed in claim 1, wherein the citric acid, the succinic acid or the salt thereof is contained in an amount of from 0.1 to 1000 mM.

3. The enzyme substrate as claimed in claim 1, which is a substrate for an alkaline phosphatase.

4. The enzyme substrate as claimed in claim 1, which is an aqueous solution.

5. The enzyme substrate as claimed in claim 1, which is a dry material.

6. A reagent kit for an enzyme activity assay which comprises the enzyme substrate according to claim 1.

7. A reagent kit for an immunoassay using an enzyme as a label which comprises the enzyme substrate according to claim 1.

8. A method for stabilizing a phosphoric ester selected from 4-methylumbelliferone phosphoric acid or p-nitrophenylphosphoric acid or a salt thereof which comprises maintaining the phosphoric ester in contact with at least one of citric acid and succinic acid or a salt thereof.

9. The method as claimed in claim 8, wherein the citric acid, the succinic acid or the salt thereof is present in an amount of from 0.1 to 1000 mM.

10. A method for producing a stabilized phosphoric ester selected from 4-methylumbelliferone phosphoric acid or p-nitrophenylphosphoric acid or a salt thereof which comprises adding to the phosphoric ester at least one of citric acid, succinic acid or a salt thereof.

11. The method as claimed in claim 10, wherein the citric acid, the succinic acid or the salt thereof is added in an amount of from 0.1 to 1000 mM.

* * * * *